(12) United States Patent
Locke

(10) Patent No.: US 6,717,311 B2
(45) Date of Patent: Apr. 6, 2004

(54) COMBINATION MAGNETIC RADIAL AND THRUST BEARING

(75) Inventor: Dennis H. Locke, Schenectady, NY (US)

(73) Assignee: Mohawk Innovative Technology, Inc., Albany, NY (US)

( * ) Notice: Subject to any disclaimer, the term of this patent is extended or adjusted under 35 U.S.C. 154(b) by 0 days.

(21) Appl. No.: 09/881,114

(22) Filed: Jun. 14, 2001

(65) Prior Publication Data

US 2003/0193252 A1 Oct. 16, 2003

(51) Int. Cl.[7] ............................................. F16C 39/06
(52) U.S. Cl. ....................... 310/90.5; 623/3.13; 417/356
(58) Field of Search ........................... 310/90.5, 181, 310/180; 600/16, 17; 417/423.7, 423.1, 423.3, 356, 423.12; 623/3.11, 3.13

(56) References Cited

U.S. PATENT DOCUMENTS

| | | | |
|---|---|---|---|
| 4,763,032 A | * | 8/1988 | Bramm et al. ............. 310/90.5 |
| 4,944,748 A | | 7/1990 | Bramm et al. |
| 5,078,741 A | | 1/1992 | Bramm et al. |
| 5,084,643 A | | 1/1992 | Chen |
| 5,133,527 A | | 7/1992 | Chen et al. |
| 5,175,457 A | | 12/1992 | Vincent |
| 5,202,824 A | | 4/1993 | Chen |
| 5,385,581 A | | 1/1995 | Bramm et al. |
| 5,443,503 A | * | 8/1995 | Yamane ..................... 623/3.14 |
| 5,521,448 A | | 5/1996 | Tecza et al. |
| 5,541,460 A | * | 7/1996 | Dunfield et al. .......... 310/67 R |
| 5,574,322 A | * | 11/1996 | Nii et al. ................... 310/90.5 |
| 5,666,014 A | | 9/1997 | Chen |
| 5,928,131 A | * | 7/1999 | Prem ........................... 600/16 |
| 6,201,329 B1 | * | 3/2001 | Chen ........................ 310/90.5 |
| 6,259,179 B1 | * | 7/2001 | Fukuyama et al. ........ 310/90.5 |
| 6,363,276 B1 | * | 3/2002 | Prem et al. ..................... 607/6 |

* cited by examiner

Primary Examiner—Karl Tamai
Assistant Examiner—Leda T. Pham
(74) Attorney, Agent, or Firm—James C. Simmons

(57) ABSTRACT

A magnetic bearing wherein axially spaced combinations of permanent magnets on a rotor and stator are polarized to levitate the rotor and positioned with the rotor magnets offset axially outwardly (or inwardly) of the stator magnets to allow a force balance to be achievable to bear axial thrust. An electrically energizable coil modulates magnetic flux between the respective stator and rotor magnets for each combination. A first electrical circuit regulates electrical energy to the coils for maintaining a reference position of the rotor. A second electrical circuit compares feed-back of electrical energy to at least one of the coils with a reference electrical energy of about zero amps or volts and integrates the differences until the difference is about zero to provide a signal to modify the reference position, whereby to attain a zero force balance position wherein the current which must be supplied to the coils may be reduced to near zero.

18 Claims, 4 Drawing Sheets

COMBINATION MAGNETIC RADIAL AND THRUST BEARING

The present invention relates generally to magnetic bearings which may be used, for example, to bear the rotor of a blood pump which is implanted into the human body to assist the heart. Magnetic bearings are ideally suited for a blood pump since they allow the rotor to be suspended relative to the stator and therefore allow free flow of blood without obstructions so that it does not stagnate and thus coagulate and allow the blood to flow along a path large enough that individual blood cells are not damaged due to shear.

Bearings for blood pumps as well as other pumps and motors must not only bear the rotor radially (journal bearing) but must also bear the rotor axially (thrust bearing). Reliable axial control of the rotor is particularly important in blood pumps since too much movement of the rotor axially may narrow a blood pathway thereby restricting blood passage so much that individual blood cells may become damaged due to shear and the blood may coagulate. In addition, it is important that the power consumption in blood pumps be low since the heat resulting from high power consumption may damage or destroy blood cells, and low power consumption is also desirable to reduce the operating costs.

Patents (in addition to those cited hereinafter) which may be of interest in the development of magnetic bearings include U.S. Pat. Nos. 5,084,643; 5,133,527; 5,202,824; 5,666,014; 5,175,457; and 5,521,448, which above patents are hereby incorporated herein by reference.

An example of radial and axial magnetic bearings for blood pumps is found in U.S. Pat. No. 6,201,329 which is assigned to the assignee of the present invention and which is hereby incorporated herein by reference. This application discloses a blood pump wherein permanent magnetic rings are provided in attraction on opposite sides of each of two axially spaced radial gaps to levitate the rotor, and an actively controlled magnetic means is provided across radial gaps to bear thrust.

While the above blood pump bearings are considered to work well, it is nevertheless considered desirable to simplify the magnetic bearing arrangement so as to provide a more compact blood pump as well as to reduce manufacturing cost. It is also considered desirable to reduce the bearing operating cost.

U.S. Pat. Nos. 4,944,748; 5,078,741; and 5,385,581 to Bramm et al disclose a magnetically suspended and rotated rotor having an axially polarized cylindrical permanent magnet at each end of the rotor. An axially polarized permanent magnet ring is provided at each end of the stator to magnetically interact therewith respectively to levitate the rotor. The stator magnet rings are offset axially outwardly of the rotor magnets respectively. An Electromagnet exerts a control force on the rotor magnets to keep the impeller at the null position, in the absence of additional static axial forces on the impeller. The electromagnet receives feed-back of rotor position (see col. 14, last paragraph, of the '581 patent) to maintain the null position. As seen in FIG. 4 of the '581 patent, it appears that one pole of the rotor magnet is used to levitate the rotor and the electromagnet flux interacts with the other pole to act as a thrust bearing. It is believed that this does not allow an arrangement of magnets to achieve a desired radial and angular stiffness to suitably support the rotor, with the result that the specific gravity of the fluid determines the rotor design (see the paragraph which spans cols. 26 and 27 of the '581 patent) so that the rotor may not be able to levitate and spin without the presence of fluid.

When additional static axial forces are applied to the impeller of the above pump, as detected by the electronic circuitry, a different equilibrium position is thereafter maintained, instead of the null or previous equilibrium position (see the paragraph which spans cols. 11 and 12 of the '581 patent). As discussed in the paragraph which spans cols. 22 and 23 of the '581 patent, if an additional axial force is exerted on the impeller, this is detected by signals, provided to a difference amplifier by the position sensors, having a direct current component which is said to arise from a persistent small shift in the impeller position as opposed to random variations in impeller position about the null position. Thus, a new equilibrium position is established in response to these direct current component signals. Not only is such a system which uses displacement as feedback for establishing a new equilibrium position complex but it is also unreliable (prone to error) since there may be instances in which it may be difficult for the circuitry to "tell" whether there is an outside axial force or just instability causing a change in impeller position.

It is accordingly an object of the present invention to provide a simplified, compact, and reliable magnet assembly for the radial and thrust bearings for a rotor.

It is a further object of the present invention to provide low power consumption for such a magnet assembly.

In order to provide a simplified, compact, and reliable magnet assembly for the radial and thrust bearings for a rotor, in accordance with the present invention, first and second axially spaced combinations are provided each including at least one permanent magnet disposed on each of the rotor and stator and polarized to levitate the rotor, and there is further provided an electrically energizable coil for modulating flux between the respective stator and rotor magnets, and the rotor magnets are offset axially both inwardly or both outwardly of the stator magnets respectively.

In order to provide low power consumption for such a magnet assembly, in accordance with a preferred embodiment of the present invention, an electrical circuit responsive to feed-back of electrical energy to at least one of the coils is provided for comparing thereof with a reference electrical energy and integrating the differences therebetween to provide a signal to modify a reference position of the rotor, whereby to attain a zero force balance position wherein the current to the coils may be reduced to near zero.

The above and other objects, features, and advantages of the present invention will be apparent in the following detailed description of the preferred embodiment thereof when read in conjunction with the accompanying drawings wherein the same reference numerals denote the same or similar parts throughout the several views.

DETAILED DESCRIPTION OF THE PREFERRED EMBODIMENT

Figure 1:
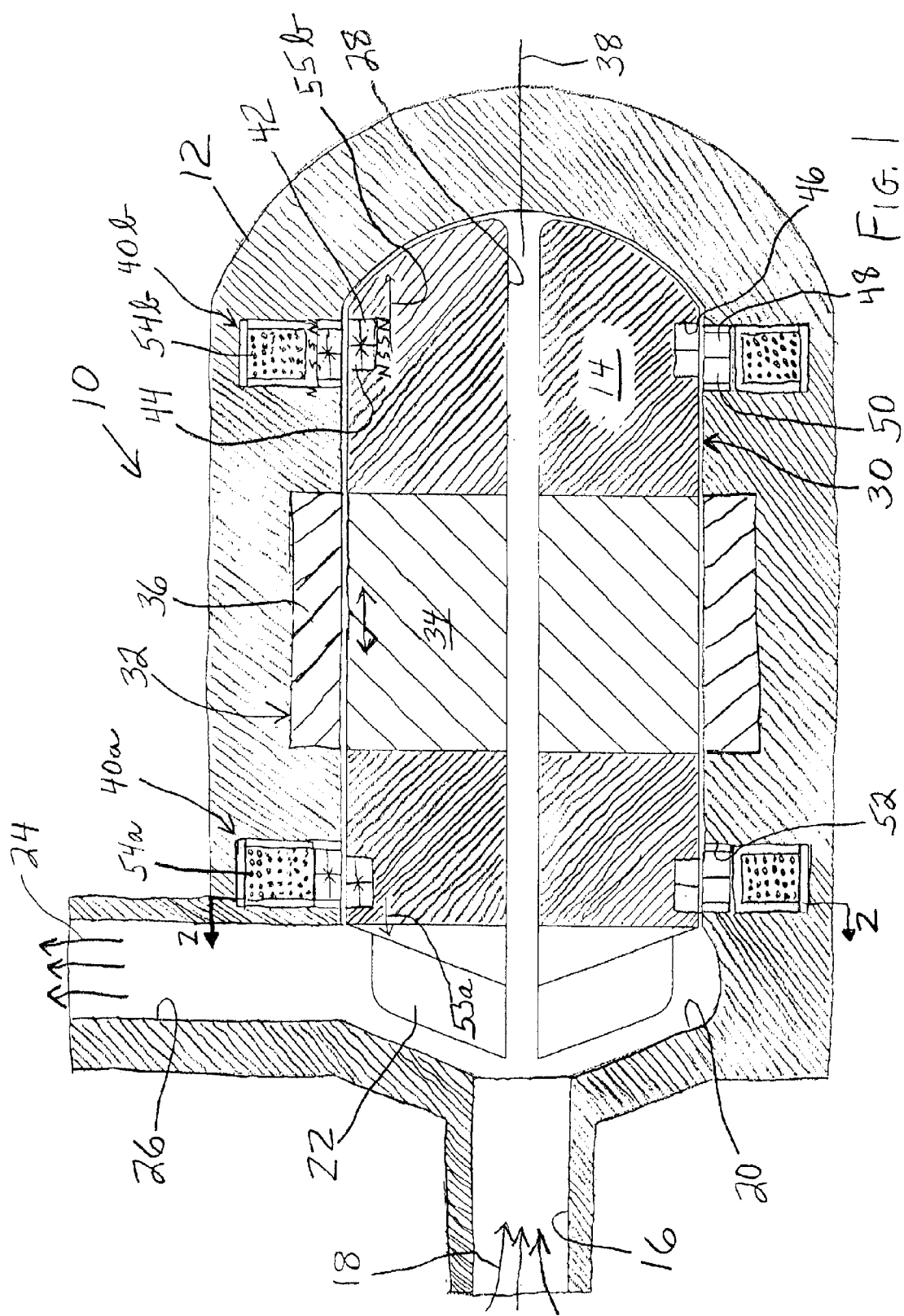
FIG. 1 is a sectional schematic view illustrating a pump which embodies the present invention.
Figure 2:
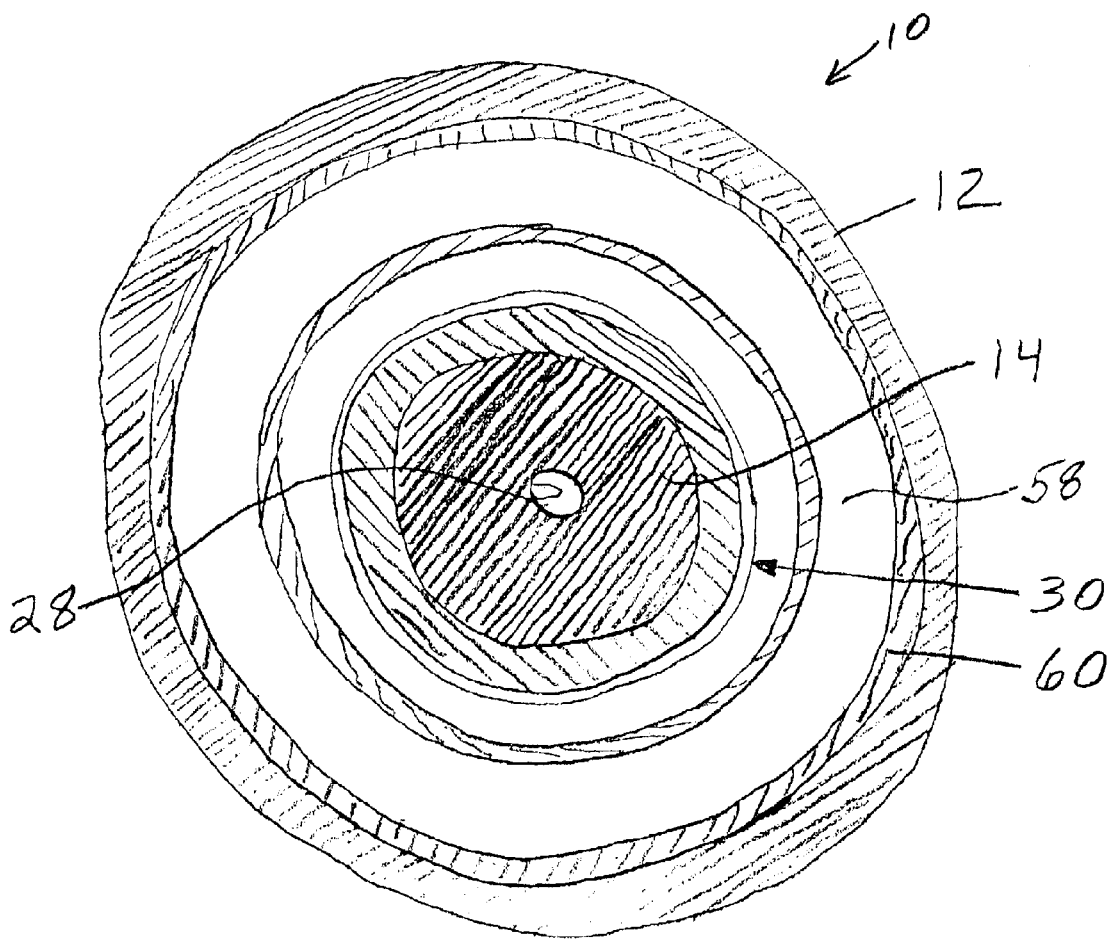
FIG. 2 is a sectional view thereof taken along lines 2—2 of FIG. 1.
Figure 3:
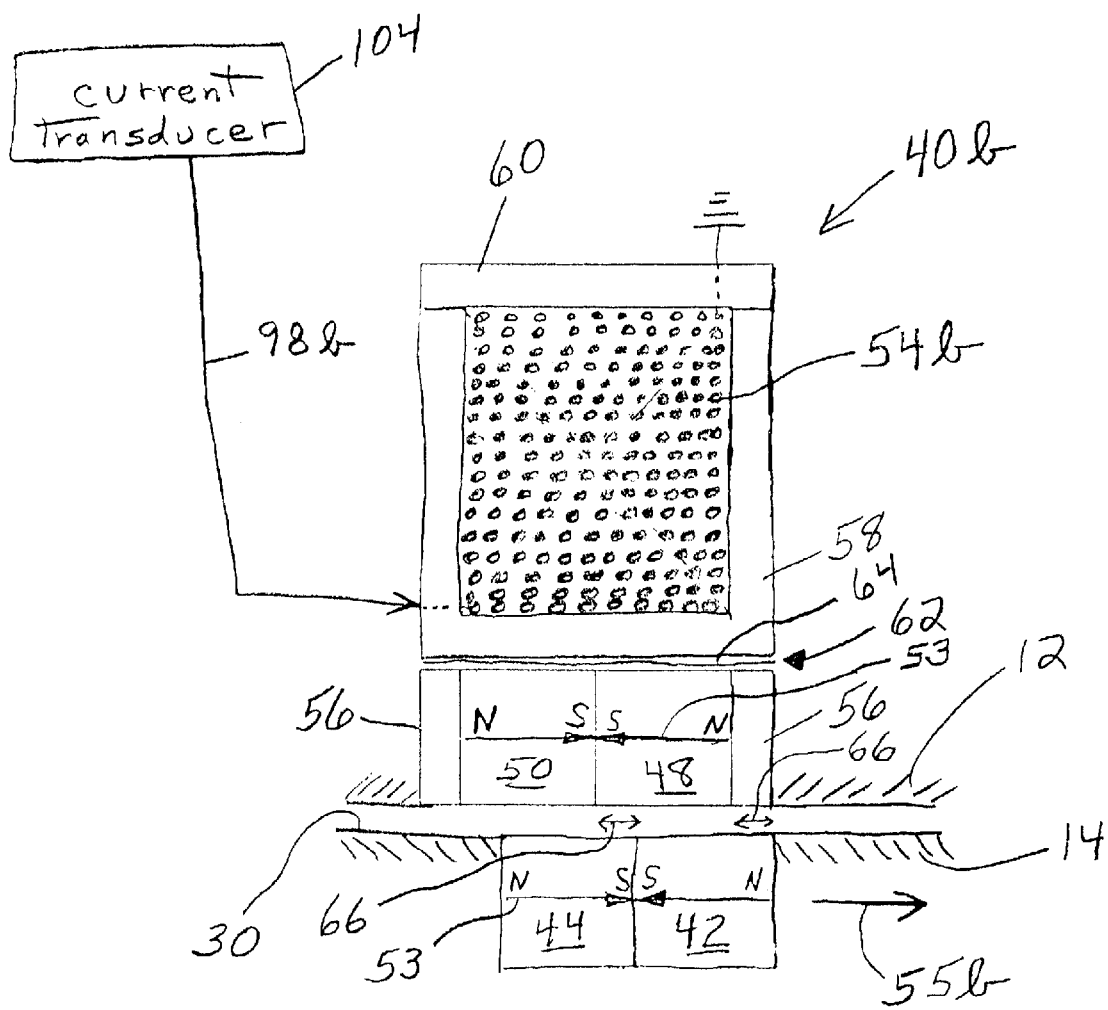
FIG. 3 is a detail view of a portion thereof.

Referring to FIGS. 1 to 3, there is shown generally at 10 a pump which may be implanted into the human body to assist the heart in pumping blood through the circulatory system. However, it should be understood that a pump in accordance with the present invention may have other uses. Likewise, the bearing discussed hereinafter can be applied to other machinery having a rotatable shaft. The pump 10 has a housing 12 and a rotor 14 which is rotatably received within the housing 12. Although the housing and rotor are shown schematically as single sections for ease of illustration, it should be understood that each of them would in practice be composed of sections suitably joined together to allow assembly and to allow various components discussed hereinafter to be mounted thereon, and such mounting of components and assembly of the pump can be done using principles commonly known to those of ordinary skill in the art to which the present invention pertains. All materials with which the blood or other fluid comes into contact are composed of a material which is biocompatible with the blood/fluid or are suitably coated with a suitable biocompatible material such as, for example, titanium.

The housing 12 has a centrally disposed opening, illustrated at 16, at an end axially thereof defining an inlet for receiving blood or other fluid into the pump, as illustrated at 18. The blood flows into an impeller chamber, illustrated at 20, in which is contained an impeller 22. The blood is discharged, as illustrated at 24, from the impeller chamber 20 via an outlet, illustrated at 26, extending tangentially from the housing 12, as is conventionally known in the art.

The impeller 22 is rotatably driven for forcing the blood through the pump by a suitable motor 32 comprising a suitable magnet assembly, illustrated at 34, on the rotor 14 and a suitable stator coil assembly 36 in the housing 12. The motor assembly 32 can be of any conventional construction, for example, brushless direct current, suitable for effecting rotation of the rotor. While the rotor is shown as being received within the stator or housing, the rotor may if desired be doughnut-shaped and rotate about a stator received therein, as shown in the aforesaid U.S. Pat. No. 6,201,329. The rotor 14 is magnetically suspended, as discussed hereinafter, for rotation about its rotational axis, illustrated at 38.

Radial and thrust loads on the rotor are borne by a pair of axially spaced combinations 40 (i.e., 40a and 40b). One combination 40a is at one end axially of the rotor and the other combination 40b is at the opposite end axially of the rotor. Each combination 40 comprises a pair of axially polarized side-by-side permanent magnet rings 42 and 44 received in a circumferential groove 46 in the radially outer surface of the rotor 14. The rotor magnet rings 42 and 44 are polarized in opposite directions, as illustrated by arrows 54 (each showing polarization from the North to the South pole of the respective magnet), i.e., the South poles thereof are shown in the drawings to face each other. A similar pair of axially polarized side-by-side permanent magnet rings 48 and 50 are received in a circumferential groove 52 in the radially inner surface of the housing 12. The stator magnet rings 48 and 50 are also polarized in opposite directions, i.e., the South poles thereof are shown in the drawings to face each other. Each combination 40 also includes an electrically energizable coil 53 (i.e., coils 54a and 54b for combinations 40a and 40b respectively) received in the housing 12 radially outwardly of the respective pair of magnet rings 48 and 50, each coil 54 being wound as a toroid over the respective pair of magnet rings 48 and 50 (i.e., the magnetic rings 48 and 50 are disposed within the toroid defined by the respective coil 54) to provide magnetic flux which interacts with the magnetic flux of the rotor and stator magnet rings 42, 44, 48, and 50, as will be described more fully hereinafter.

Blood flows in the space or gap, illustrated at 30, between the rotor 14 and housing 12 for wash flow and cooling the motor and axial magnetic bearing coils 36 and 54 respectively, and the blood return flow path is via a central rotor passage, illustrated at 28. As will become more apparent hereinafter, this gap 30 is devoid of obstructions which would undesirably cause the blood to coagulate, and the gap thickness is large enough, at least about 0.020 inch, so that individual blood cells are not damaged due to shear.

The rotor magnets 42 and 44 are aligned in repulsion with the stator magnets 48 and 50 respectively, i.e., like poles thereof face each other across the gap 30 in repulsion. This polarization in opposition or repulsion creates a radial force to levitate the rotor 14. It is necessary to have both of the axially spaced combinations 40a and 40b of such magnets in order to achieve stability radially.

In order to achieve acceptable angular and axial stability, the rotor magnets 42 and 44 are offset axially outwardly from the stator magnets 48 and 50 respectively thereby creating axial forces in opposite directions (each axially outwardly), as illustrated at 55a and 55b respectively. The opposition in axial forces 55a and 55b allows a zero force balance to be attainable. The current direction and magnitude in the coils 54a and 54b will vary their magnetic flux which in turn, due to interaction of the coil magnetic flux with the magnetic flux between the stator and rotor magnets, will vary the axial forces 55a and 55b respectively to achieve stability at the zero force balance position of the rotor 14. The coils 54a and 54b may be connected in series or parallel, thereby sharing the same magnitude of current; however, the flux of one coil 54a must be 180 degrees out of phase with the flux of the other coil 54b such as by the direction of current in one coil being opposite the direction of the current in the other coil, as described hereinafter with respect to FIG. 4.

The rotor 14 and housing 12 are preferably composed of a non-magnetic material such as, for example, aluminum, titanium, non-magnetic stainless steel, and ceramic. If either the rotor or the housing is made of magnetic material, then spacer pieces of non-magnetic material should be provided adjacent the magnets and over a distance therefrom, for example, over a distance of about ¼ inch or more therefrom, so that the magnetic material of the rotor or housing does not interfere with the magnet flux. Whatever material is used, it of course must also be biocompatible with the blood to be pumped if the pump is to serve as a blood pump. Mechanical stops (not shown) may desirably be provided to limit rotor axial movement to, for example, about 0.005 inch to prevent rotor damage in case of bearing break-down.

One of the problems encountered in developing the magnet combinations 40 was the difficulty in maintaining the necessary radial stiffness while modulating the axial forces 55 to maintain the zero force balance. It was found that by placement of magnetic material around the coils 54 and adjacent the sides of the stator magnets 48 and 50 and by providing an air gap between the magnetic material surrounding the coil and the stator magnets 48 and 50, magnetic flux may suitably be shunted away from between the stator and rotor magnets in such a way as to be able to modulate the axial force substantially while producing only a minimal effect on radial stiffness. Thus, in accordance with a preferred embodiment of the present invention, a pair of magnetic material rings 56 are disposed in contacting relation with the outer sides of the magnet rings 48 and 50 respectively, a generally U-shaped channel ring 58 of magnetic material is disposed to receive each coil 54 and a cap ring 60 of magnetic material is tightly fitted (may, for example, be welded) to each ring 58 to enclose the respective coil 54, and an air gap, illustrated at 62, is provided between the magnetic material 58 and the stator magnets 48 and 50 for each combination 40. The magnetic material for each of the rings 56, 58, and 60 may, for example, be Carpenter-BFM material, which is easily machinable. By "air gap" is meant a space filled with air or non-magnetic material. For example, the air gap 62 is shown in FIG. 3 to comprise spacer or filler strips or shim stack 64 of plastic material.

The following example is for illustrative purposes only and not for purposes of limitation. For example, each of the magnet rings 42, 44, 48, and 50 may be grade 35 neodidium-iron-boron magnets which are about 0.1 inch square in section (or otherwise suitably sized for the desired radial stiffness), and the rings 56, 58, and 60 may each have a thickness of about 0.03 inch. The rotor magnets 42 and 44 may be offset a distance axially, illustrated at 66, of, for example, about 0.03 inch from the stator magnets 48 and 50 respectively. If the width of the air gap 62 is too great, it was found that it took too many ampere-turns to get the desired change in axial force, but if the width thereof is too small, it was found that the radial stiffness would be reduced too much because too much flux was being shunted away from between the stator and rotor magnets. It was therefore concluded that a gap thickness of, for example, about 0.01 inch was a good compromise between the extremes. It was found that with the above combination, the coil current could be changed to vary the axial force for effective stable control without the radial force changing much. For example, without current being supplied to the coil 54, the axial and radial force measurements were 706 and 601 newton-meters respectively, yet when a current of 3 amperes were applied to the coil 54, the axial force measurement increased to 764 newton-meters while the radial force measurement desirably stayed about the same at 597 newton-meters.

Figure 4:
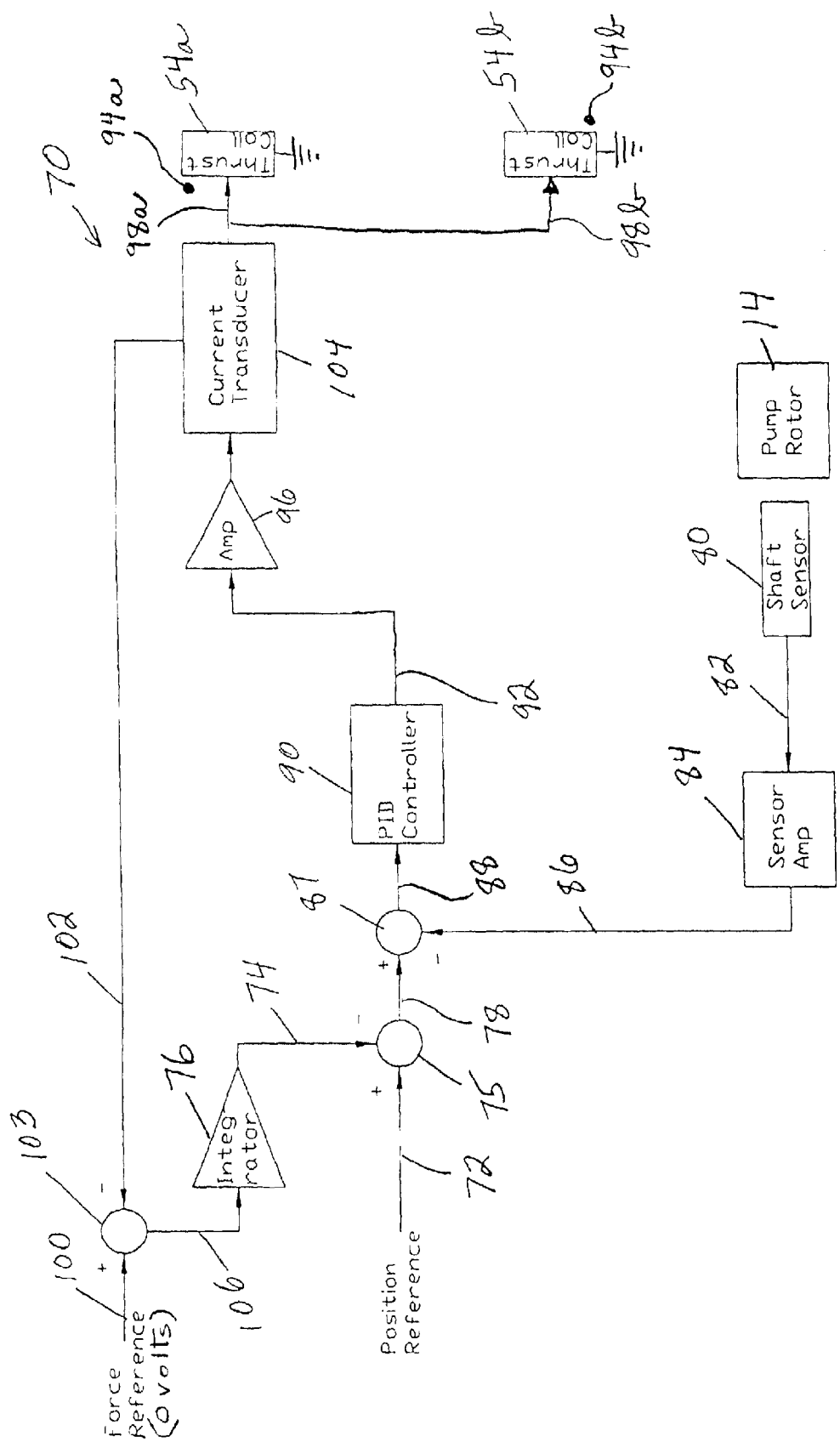
FIG. 4 is a schematic view of the control circuitry therefor.

Referring to FIG. 4, there is illustrated generally at 70 a control system for the bearing 40. A position reference signal, illustrated at 72, as modified by signal 74 from integrator 76 to provide signal 78 as discussed hereinafter, establishes the running position (control position) of the rotor 14. A suitable sensor 80 is provided to measure the rotor axial position and provide a signal 82 which is suitably amplified by amplifier 84, and the amplified signal 86 is compared in comparator 87 with the modified position reference signal 78. The resulting summed signal 88 is sent to a PID (proportional-integral-differential) controller 90 which is conventionally known in the art and is described and illustrated in U.S. Pat. Nos. 5,202,824 and 5,084,643, which are incorporated herein by reference. Based on the feed-back of rotor position as indicated by the magnitude of the signal 88, the PID controller 90 outputs a signal (voltage) along line 92 for correcting rotor axial position error. The output voltage 92 is directed to amplifier 96 which produces a current which is directed to thrust coils 54a and 54b through lines 98a and 98b, the coils 54a and 54b being wound so that the direction of current through one line 98a is opposite to the direction of the current through the other line 98b (as indicated by dots 94a and 94b respectively) so that the flux of one coil is 180 degrees out of phase with the flux of the other coil in order to provide a push-pull control to the coils 54a and 54b respectively to maintain stability of the rotor 14.

An outside force on the rotor 14 will cause it to begin moving axially away from a running or control position. If we disregard the modification due to signal 74 so that the signal 78 is the same as signal 72, then the running or control position is defined by the preselected position reference signal 72 and may be the magnet null position defined by the permanent magnets 42, 44, 48, and 50 when no axial forces are acting thereon. The change in rotor position is detected by sensor 80, and the unmodified position reference signal 72 is combined with sensor amplified signal 86 by comparator 87 to provide a difference signal 88 (error signal) to PID controller 90 which in response outputs a signal along line 92 to effect a suitable interaction between the coils 54 and the permanent magnets to return the rotor to the running or control position. With the signal 72 so unmodified, the system 70 is a conventional system for controlling rotor axial position.

When the outside force is more than momentary, energy is undesirably expended in supplying the electrical energy to continually counteract it so as to maintain the preselected running or control position (as set by the position reference signal 72). In accordance with a preferred embodiment of the present invention, new running or control positions (modified position references) are set in response to increases in the current 98 to the coils 54, and these modified running or control positions are positions (if only momentary) of axial force equilibrium wherein axial force acting on the rotor is balanced by axial force supplied by the magnets. Such positions of axial force equilibrium are referred to herein as "zero force balance positions." In other words, the current to the coils can be reduced to zero at the rotor axial position wherein there is zero net axial force acting on it, i.e., a zero force balance or equilibrium position. As a result, the amount of current needed to maintain these modified running or control positions is near zero. Thus, the current transducer 104 outputs a voltage to line 102 which is representative of the current flowing in the coils 54a and 54b. A force reference signal 100 of zero volts (or other suitable small voltage) is combined in comparator 103 with voltage in line 102 from current transducer 104. The resulting difference (or error) voltage is outputted onto line 106 to integrator 76 where it is integrated and compared in comparator 75 with the position reference voltage 72 to provide a modified position reference voltage or signal 78. This integration continues until the voltage in line 106 goes to zero, which means that a new force balance or equilibrium position is attained wherein the current supplied to coils 54 by PID controller 90 is essentially zero at this new zero force balance position. It is this modified position reference signal 78 that is compared with rotor position signal 86 in comparator 87 and the difference supplied as signal 88 to PID controller 90.

While the signals in lines 100 and 102 are described above as voltages, it should be understood that the signals 100 and 102 as well as signal 74 may be other measures of electrical energy, i.e., amperes. However, the use of voltage signals is preferred since voltage signals are easier to work with. As used herein and in the claims, the term "electrical energy" is defined to include amperes and any other suitable measure of electrical energy as well as volts.

The use of the same magnets for bearing both axial and radial loads in accordance with the present invention advantageously allows greater compactness of the pump to be achieved, and the magnetic flux between the rotor and stator magnets may be modulated by use of the coil as discussed herein to achieve good radial and angular stiffness to support the rotor while maintaining axial stability. Moreover, the axial position reference is continuously re-set based on electrical energy feed-back to achieve zero force balance, whereby a minimum of current (energy) may be used to stabilize the bearing thereby to prevent blood damage due to heat as well as to provide more economical operation.

It should be understood that, while a preferred embodiment of the present invention has been described in detail herein, the invention can be embodied otherwise without departing from the principles thereof. For example, it is envisioned that the rotor and corresponding stator magnets may be polarized in attraction, or that the rotor magnets may be offset to the inside of the stator magnets. For another example, each of the magnets may be polarized radially. For yet another example, any number of rotor and stator magnets may be provided for each bearing combination, i.e., 1 rotor and 1 stator magnet for each bearing combination. Such other embodiments are meant to come within the scope of the present invention as defined by the appended claims.

What is claimed is:

1. Apparatus comprising a rotor, a stator, first and second axially spaced combinations each including at feast one permanent magnet disposed on each of said rotor and said stator on opposite sides of a respective axially extending gap portion and polarized to levitate said rotor and further including an electrically energizable coil wound as a toroid over said respective at least one stator magnet and with said respective at least one rotor magnet disposed substantially within the toroid for modulating magnetic flux between said respective stator and rotor magnets, electrical circuitry for regulating electrical energy to said coils for stabilizing said rotor axially, and said rotor magnets being offset axially of said stator magnets respectively such that said rotor magnets are offset axially inwardly of said corresponding stator magnets or such that said rotor magnets are offset axially outwardly of said corresponding stator magnets.

2. Apparatus according to claim 1 wherein said electrical circuitry includes a first circuit for regulating electrical energy to said coils for maintaining an axial reference position of said rotor and a second circuit responsive to feed-back of electrical energy to at least one of said coils for modifying said axial reference position.

3. Apparatus according to claim 2 wherein said second circuit includes a comparator for comparing electrical energy to at least one of said coils with a reference electrical energy and an integrator of the differences therebetween.

4. Apparatus according to claim 3 wherein said reference electrical energy is about zero volts.

5. Apparatus according to claim 1 wherein said circuitry includes a rotor position sensor, a comparator for outputting a difference signal between a signal from said sensor and a position reference signal, and a PID controller for receiving said difference signal and outputting electrical energy to said coils in response to said difference signal.

6. Apparatus according to claim 1 wherein said rotor magnets are offset axially outwardly of said stator magnets respectively.

7. Apparatus according to claim 1 wherein said rotor magnets are magnetized to repel said stator magnets respectively.

8. Apparatus according to claim 1 wherein said magnets are axially polarized.

9. Apparatus according to claim 1 wherein said magnets are magnet rings.

10. Apparatus according to claim 1 wherein each of said combinations comprises two of said rotor magnet which are polarized axially in opposite directions and two of said stator magnet which are polarized axially in opposite directions.

11. Apparatus according to claim 1 wherein said coil is positioned on said stator.

12. Apparatus according to claim 1 further comprising magnetic material in surrounding relation to said coil.

13. Apparatus according to claim 12 wherein said coil is positioned on said stator, the apparatus further comprising means defining an air gap between said magnetic material and said respective stator magnet.

14. Apparatus according to claim 13 further comprising magnetic material disposed alongside said stator magnet.

15. Apparatus comprising a rotors a stator, first and second axially spaced combinations each including at least one permanent magnet disposed on each of said rotor and said stator on opposite sides of a respective axially extending gap portion and polarized to levitate said rotor and further including an electrically energizable coil for modulating magnetic flux between said respective stator and rotor magnets, a first electrical circuit for regulating electrical energy to said coils for maintaining a reference position of said rotor, and a second electrical circuit responsive to feed-back of electrical energy to at least one of said coils for modifying said reference position, wherein said second circuit includes a comparator for comparing electrical energy to at least one of said coils with a reference electrical energy of about zero and further includes an integrator of the differences therebetween.

16. Apparatus according to claim 15 wherein said rotor magnets are offset axially outwardly of said stator magnets respectively.

17. Apparatus according to claim 15 wherein said coil is positioned on said stator, the apparatus further comprising magnetic material in surrounding relation to said coil, means defining an air gap between said magnetic material and said respective stator magnet, and magnetic material disposed alongside said stator magnet.

18. A method for bearing a rotor comprising providing first and second axially spaced combinations each including at least one permanent magnet disposed on each of the rotor and a stator on opposite sides of a respective axially extending gap portion and polarized to levitate the rotor, providing an electrically energizable coil for each of the combinations, regulating electrical energy to the coils for maintaining a reference position of the rotor, and modifying, in response to feed-back of electrical energy to at least one of the coils, the reference position, wherein the step of modifying the reference position comprises comparing electrical energy to at least one of the coils with a reference electrical energy, integrating the differences therebetween until a difference of about zero is attained, and selecting the amount of reference electrical energy to be about zero.

* * * * *

UNITED STATES PATENT AND TRADEMARK OFFICE
CERTIFICATE OF CORRECTION

PATENT NO.    : 6,717,311 B2
DATED         : April 6, 2004
INVENTOR(S)   : Locke It is certified that error appears in the above-identified patent and that said Letters Patent is hereby corrected as shown below:

<u>Column 7,</u>
Line 18, "feast" should read -- least --.

<u>Column 8,</u>
Line 17, "rotors" should read -- rotor, --.

Signed and Sealed this

Twenty-third Day of November, 2004

JON W. DUDAS
*Director of the United States Patent and Trademark Office*